United States Patent [19]

Galfrè et al.

[11] 4,350,683

[45] Sep. 21, 1982

[54] ANTIBODY PRODUCTION FROM HYBRID CELL LINE

[75] Inventors: Giovanni Galfrè; Cesar Milstein, both of Cambridge; Bruce W. Wright, Comberton, all of England

[73] Assignee: National Research Development Corporation, London, England

[21] Appl. No.: 109,391

[22] Filed: Jan. 3, 1980

[30] Foreign Application Priority Data

Jan. 9, 1979 [GB] United Kingdom ............... 7900775

[51] Int. Cl.³ ................. C12P 21/00; C12N 15/00; C12N 5/00
[52] U.S. Cl. ......................... 424/85; 424/12; 435/7; 435/172; 435/240; 435/68
[58] Field of Search ............. 435/68, 172, 240, 241, 435/7; 424/85, 86, 12

[56] References Cited

U.S. PATENT DOCUMENTS 4,172,124  10/1979  Koprowski et al. ............ 435/240 X
4,196,265   4/1980  Koprowski et al. ............ 424/85 X

OTHER PUBLICATIONS

Galfre, et al., Antibodies to Major Histocompatibility Antigens Produced by Hybrid Cell Lines, Nature, vol. 266, 1977, (pp. 550–552).
Cotton, et al., Fusion of Two Immunoglobulin Producing Myeloma Cells, Nature, vol. 244, 1973 (pp. 42–43).
Kohler, et al., Continuous Cultures of Fused Cells Secreting Antibody of Predefined Specificity, Nature, vol. 256, 1975 (pp. 495–497).
Galfre, et al., RatxRat Hybrid Myelomas and a Monoclonal Anti–Fd Portion of Mouse IgG, Nature, vol. 277, 1979, (pp. 131–133).

*Primary Examiner*—David M. Naff
*Attorney, Agent, or Firm*—Oblon, Fisher, Spivak, McClelland & Maier

[57] ABSTRACT

Hybrid cell lines for providing antibodies are produced from a rat myeloma cell line having the C.N.C.M. designation I-078. In production of the hybrid cells, the rat myeloma cell line is fused with immunocyte cells such as spleen cells from an animal such as a rat sensitized to an immunogen. Use of the rat myeloma cell line is particularly advantageous for in vivo cultivation of a hybrid cell line to produce antibodies.

15 Claims, No Drawings

ANTIBODY PRODUCTION FROM HYBRID CELL LINE

This invention relates to cell lines and to their use in the production of antibodies.

The production of antibodies from cell lines derived by cell fusion techniques from an appropriate parental cell line has recently received attention. The method has been used with one of several mouse myeloma cell lines as the parent cell line which is fused with cells from immunised mice or rats to give a hybrid myeloma which is then grown to thereby produce antibodies against the immunogen used in the immunisation. The particular advantage of this method is that it may be used for the production of highly specific antibodies using non-purified immunogens. Although the method has provided an important new tool for use in immunology it has until now suffered from certain limitations arising from the nature of the parental cell lines available.

It is an object of the present invention to provide a new cell line for use in the preparation of monoclonal antibodies having certain advantages over the mouse myeloma cell lines at present available for this purpose.

Accordingly, the present invention comprises a rat myeloma cell line having the characteristics of the cells deposited with the Collection Nationale de Cultures de Microorganisms (C.N.C.M.) under the number I-078.

The cell line of the present invention possesses several advantages over the mouse myeloma cell lines. The in vivo cultivation of a hybrid cell line for the production of antibodies has certain advantages as compared with in vitro tissue culture methods including the significantly higher levels of antibody per ml which are obtained in animal serum as compared with a culture medium. The use of the rat for the in vivo culture is to be preferred to the use of the mouse on several counts, for example the yield of serum and ascitic fluid is higher, litters are generally larger, and rats may respond better than mice to antigenic stimulation. Moreover, rats are required for the production of monoclonal xenogenic anti-mouse and allogenic anti-rat antibodies but we have found that the hybrid cells produced by the combination of cells from immunised rats with a parent mouse myeloma cell line are not readily cultivated in either mice or rats. In addition, the rat cell line of the present invention may have advantages in certain heterologous fusions such as those with rabbit or human cells.

Although a rat myeloma cell line has been described in the literature, we found this to be quite unsuited for use as a parent cell line in the production of monoclonal antibodies, and it was necessary to subject this cell line to an extensive process of selection and/or mutation in order to produce the cell line of the present invention. The starting point for the preparation of the present cell line was the 8-azaguanine resistant mutant, 210.RCY3-.Ag1, of the rat myeloma tumour S210 (Cotton and Milstein, Nature, 1973, 244, 42). This mutant was initially tested for its ability to fuse with normal or immunised rat spleens and gave disappointing results. The cells were nevertheless subcloned twice in soft agar and the clone Y3-Ag1.2.3. was finally selected for further study, this giving no revertants when batches of $10^7$ cells were tested. The fusion efficiencies of this clone were initially still unsatisfactory, however, and it was therefore grown continuously in a spinner flask and tested for fusion efficiency at different times. It was only after a period of five months cultivation including periods at both low and high cell densities that the cell line of the present invention showing good fusion characteristics was obtained. A reserve stock of this cell line designated as Y3-Ag1.2.3. is held at the MRC's Laboratory of Molecular Biology and, additionally, the cell line was desposited with the Collection Nationale de Cultures de Microorganisms (C.N.C.M.) at the Institut Pasteur in Paris on 9th January 1979, this deposit being identified by the C.N.C.M. number I-078.

The cell line of the present invention has the same general morphology as the parent line 210.RCY3.Ag1, comprising small nonround cells which tend to grow in clumps but with generally better growth characteristics than the parent. Moreover, like the parent line, it is resistant to 8-azaguanine (10 $\mu$hg/ml), it produces and secretes a unique light chain of type kappa code named S210, and it dies in medium containing hypoxanthine/aminopterin/thymidine (HAT) (Littlefield, Science, 1964, 145, 709). The line does of course also possess the particular additional property that it will undergo successful fusion with rat spleen cells at a good level of efficiency which lies generally in the range of 1 per $10^4$ to $10^6$ cells. The cells of the rat cell line number I-078 are much smaller in appearance than the mouse P3-X63-Ag8 myeloma cells, the earlier stages of growth being less obvious under the microscope. (This is also true for some but not all of the hybrid cells derived from cells I-078.) The clonability of the rat cell line in soft agar is good, the line and its ratrat hybrids generally giving rise to rather diffuse clones as compared with the tight ones given by the mouse line and its mousemouse hybrids.

The cells number I-078 may be stored in liquid nitrogen and may be grown in various forms of nutrient culture medium. Accordingly, the present invention extends to a cell culture system comprising the rat myeloma cell line having the characteristics of the cells deposited with the C.N.C.M. under the number I-078 in a nutrient culture medium therefor. Such a cell-culture system is conveniently an in vitro one, the culture medium being an essentially synthetic medium although it may of course contain ingredients obtained from a natural source such as serum. Examples of such culture media are Dulbecco's modification of Eagle's minimum essential medium (available, for instance, from Gibco Biocult Ltd., Paisley, Scotland) with a serum supplement such as 10% or less of foetal calf or heat inactivated horse serum or alternatively using the Iscove modification containing no serum. With a minor period of adaptation the cells grown in such a medium can be grown in other media such as RPMI 1640 with foetal calf serum and various other media commonly used in cell culture and described in the literature of this art.

The cell line of the present invention is a particular use in the production of hybrid cell lines which can be used for the preparation of monoclonal antibodies. The method for the production of a hybrid cell line from the parent cell line comprises fusing spleen or other immunocyte cells sensitized to an immunogen with cells of the cell line. The sensitized immunocyte cells may be taken from various sources but it has been found that the best results are obtained using rat cells rather than cells from another host such as the mouse etc. Sensitization of the immunocyte cells may occur normally, i.e. through naturally occurring immunisation but it is preferred to produce them through direct immunisation, the required immunogen being administered to the host animal. Following fusion, cloning and sub-cloning are then conveniently employed to select a suitable hybrid or hybrids.

The fusion of suitable immunocytes with the cells of the cell line generally requires admixture in a suitable medium containing an agent which promotes the fusion. The present invention thus includes a system for the fusion of cells having the characteristics of those deposited with the C.N.C.N. under the number I-078 and immunocyte cells, for example spleen cells from a mouse, or particularly a rat, in a nutrient culture medium therefor together with an agent which promotes the fusion of said cells. Such a culture medium is conveniently a synthetic one although it may of course, if desired, contain ingredients obtained from a natural source. However, such a possibility is less likely in this instance, it being preferred that serum is absent from the medium. Examples of such culture media are Eagle's minimum essential medium and its Dulbecco modification, as well as RPMI 1640 and various other media commonly used in cell culture and described in the literature of this art. Although various fusion agents may be employed, for example a virus such as Sendai virus, polyethylene glycol is preferred, for example PEG 1500. Cell fusion with these agents is documented in the literature and illustrated in the accompanying Examples but, by way of guidance, it may be indicated that from about 40 to about 55% of polyethylene glycol is often employed, the optimum concentration depending on molecular weight, for example about 50% with PEG 1500, and that if desired dimethyl sulphoxide may be added to the polyethylene glycol. The isolation of the hybrid cell line may conveniently be assisted by replacement of the original medium with HAT medium which is toxic to the parent cell line but is not in general toxic to the hybrid line.

It will be appreciated that by growing a hybrid cell line, and also the parent cell line, under certain conditions it may be possible to derive cell lines having similar useful properties to the cells from which they are derived, and that the present invention extends to the use of the cell line I-078 for the production of such derivative lines and particularly to the derivative parent cell lines and hybrids derived therefrom. The rat myeloma cell line I-078 of the present invention and most of the hybrids derived therefrom include the kappa chain S210 but it can be advantageous for the antibody produced by the hybrid not to include the immunoglobulin chain of the parental myeloma. A group of cells of particular interest is thus provided by derivative parent cell lines which no longer express the S210 kappa chain but retain the antibody secreting activity, these being produced as variants during extended culture or by more direct manipulation.

As indicated above, immunocyte cells sensitised to the required immunogen are obtainable by alternative methods. Thus, they may conveniently be obtained either by selecting naturally occurring immunocytes of the type required or by procedures described in the art comprising the administration to the animal of a series of doses of the immunogen together, where appropriate, with an adjuvant such as Fruend's adjuvant, followed by harvesting of the spleen or other immunocyte cells. The use of naturally occurring immunocytes is of particular interest in the event that the use of human immunocyte cells is considered, where administration of the immunogen may be less attractive and the immunocytes produced naturally through an infection acquired by the patient may be more suitable. An area of particular interest in relation to natural immunocytes is the production of auto antibodies.

The invention is applicable to immunocytes from directly or naturally immunised animals sensitised against a wide range of immunogens including antigens such as proteins and glyco-proteins, oligo- and polysaccharides, liposaccharides, haptens and the like, for example peptides, neuro-transmitters and hormones. Immunogens which are surface markers and which are derived from neoplastic material, particularly solid tumours, are of considerable interest but the invention may also be applied to bacterial and viral antigens and to immunogens derived from protozoa and fungi.

The present invention thus further includes cells being a hybrid between the rat myeloma cell line having the characteristics of cells deposited with the C.N.C.M. under the number I-078 and spleen or other immunocyte cells, for example from a mouse, or more particularly from a rat, sensitised to an immunogen.

The hybrid cells may conveniently be grown in the same general type of culture medium as the parent cells and as discussed hereinbefore.

For the production of the monoclonal antibodies the hybrid cells are conveniently inoculated into a rat to produce a solid or ascitic tumour. After a suitable period of growth the animal is killed and the ascites and/or serum collected for isolation of the antibody, conveniently by procedures described in the art for such a purpose. Such procedures include precipitation, dialysis, chromatography including the use of immunoadsorbents, and the use of membrane filters.

The present invention thus includes a method for the production of monoclonal antibodies which comprises inoculating a rat with hybrid cells as described hereinbefore, thereby causing a solid or ascitic tumour to grow in the rat, and thereafter isolating the antibodies from the serum or ascitic fluid of the rat.

Although such in vivo production of antibodies has certain particular advantages as described hereinbefore compared with in vitro production, there are certain uses for antibodies of an immunological rather than a chemical nature where the nature rather than the level of impurities resulting from in vivo production may mean that in vitro production is preferred. In other cases this may be necessary because the cells do not grow in vivo. Examples of suitable tissue culture procedures include massive growth in spinner containers and other known mass culture procedures which are well documented in the art. Moreover, it will be appreciated that tissue culture does have the advantage of greater simplicity of technique as compared with the use of animals but this is generally offset by the lower yields and consequently increased scale which is necessary. Generally similar purification procedures may be employed as referred to above in the case of antibodies produced by in vivo methods.

It will be appreciated that the present invention extends to antibodies whenever prepared using hybrid cells as described hereinbefore. Such antibodies have various applications in therapeutics and particularly in diagnostics, and also in such procedures as affinity chromatography. The antimouse IgG monoclonal antibody directed against the FD fragment which is described hereinafter is an example of a monoclonal antibody-producing hybrid which provides a reagent suitable as second antibody in indirect binding assays and other sandwich procedures. Other monoclonal antibodies which may be produced include antibodies to various tumour cells of human origin which recognise subpopulations of human cells and which are of potential use in haematological diagnosis. Another type of use is exemplified by the use of an antibody against a naturally occurring substance such as a protein for the purification of that substance.

The cell line of the present invention has proved to be particularly valuable for the high yield of recovery of antibody production activity. Thus, in one experiment, hybrids obtained from the cell line by fusion thereof with spleen cells of an immunised rat were analysed for their ability to secrete Ig different from the myeloma parent, this being done by SDS-PAGE analysis of the secreted products. Out of 12 cultures tested (all probably monoclonal) 11 secreted Ig chains and only one failed to secrete chains different from the myeloma parent, so that over 90% of the tested cultures secreted new immunoglobulins. Moreover, levels of at least 80% have in general been obtained with the cell line of the present invention, which is higher than the value obtained for the mouse system described by Köhler and Milstein in the European Journal of Immunology, 1976, 6, 511 which rarely gives levels higher than 50%, the overall level generally obtained being 40 to 60%.

The invention is illustrated by the following Examples.

EXAMPLES

The DMM-10% FCS used in the Examples was prepared by admixture of the following ingredients.

500 ml Dulbecco MEM (with 4500 mg glucose/liter, without sodium pyruvate. Gibco-Biocult Catalogue No. 320–1965).

5 ml sodium pyruvate MEM 100 mN (Gibco-Biocult Catalogue No. 320–1360).

10 ml Penicillin/streptomycin, 5000 units penicillin/5000 mcg streptomycin/ml. (Gibco-Biocult Catalogue No. 600–5070).

50 ml Foetal calf serum selected from different batches (Sera-Lab Catalogue No. 5000-1a).

DMM-HS and medium D are prepared similarly but with substitution of the foetal calf serum by horse serum or the omission thereof, respectively.

Example 1: Preparation of rat myeloma cell line I-078

The contents of a fresh vial of frozen 210.RCY3-Ag.1 cells was grown at 37° C. in a plastic bottle containing Eagle's minimum essential medium, Dulbecco's modification (DMM) supplemented with 10% heat inactivated horse serum (HS) and an atmosphere of 10% $CO_2$-90% air. After 3 weeks growth 500 cells, taken at logarithmic growth, were suspended in 2 ml of DMM containing 10% HS and 0.25% agar at 37° C. and the suspension was layered on 15 ml of DMM containing 10% HS and 0.5% agar solidified on a 9 cm diameter tissue culture petri dish. The cells were then incubated for 2 weeks at 37° C. in an atmosphere saturated with water and containing 7% $CO_2$ in air. The twenty fastest growing of the clones obtained were picked and transferred to culture dishes, then they were tested for their resistance to 8-azaguanine and their ability to produce and secrete the S210 light chain. On this basis, one clone (Y3-Ag.1.2) was selected and the whole procedure repeated to isolate a subclone (Y3-Ag.1.2.3).

This subclone was grown in a culture flask at 37° C. on DMM supplemented with 10% HS and when it was growing vigorously (1 week) it was transferred to a 1 l. spinner flask containing the same medium and an atmosphere of 10% $CO_2$-90% air. After 3 months of continuous growth in the spinner flask about 10 ml of the culture was placed in a culture bottle and the medium slowly replaced with DMM supplemented with 10% FCS (foetal calf serum) over a period of 2 weeks. The culture was then transferred to a spinner flask and the cells grown continuously for a further 2 months including various periods of growth at very low (about $10^4$ cells/ml) and high (about 1 to $2 \times 10^6$ cells/ml) cell densities. The fusion efficiency of the cells was tested at different stages during this process and a visible improvement was noted in the last month of growth.

At the stage of 5 months growth in the flask at 37° C. a number of samples, each containing 2 to $5 \times 10^6$ cells, were taken and frozen in the presence of 10% dimethyl sulphoxide (DMSO) and 90% FCS with a temperature gradient of about 1° C. every 2 minutes. These cells are those deposited with the C.N.C.M. under the number I-078.

Fusions are best performed using cultures grown logarithmically for at least 2 weeks. For use, cells of an original sample or from freshly prepared newly frozen stocks are rapidly thawed and diluted to 10 ml with DMM containing 10% FCS, centrifuged, resuspended in 10 ml of DMM containing 10% FCS, and grown in a culture flask as previously described in accordance with the criteria indicated above. Cultures grown for periods of over 6 months have not shown a deterioration in fusion efficiency and may even exhibit an improvement therein, but for the purposes of maintenance of the cell line without derivation storage under liquid nitrogen is used rather than continuous growth.

EXAMPLE 2

Production of hybrid between cell line I-078 and spleen cells from a rat hyperimmunised with mouse IgG Rats of the DA strain were immunised by five footpad injections at three-week intervals with 100 μg of mouse IgG in complete Freund's adjuvant and were boosted by intravenous injection of an equal amount of IgG in saline without adjuvant four days before fusion. Spleen cells from the rats were initially prepared for fusion in Dulbecco's phosphate buffered saline (PBS) containing 2% foetal calf serum (FCS). The cells were then washed with Dulbecco's modified medium in the absence of any serum supplement (medium D), and $10^8$ spleen cells were mixed with $5 \times 10^7$ cells of the cell line I-078 suspended in medium D. The mixture was centrifuged in a 50 ml plastic conical tube at 600 g for 7 minutes and the supernatant was then removed and the cell pellet disrupted by gently tapping the bottom of the tube. Further operations were performed at about 37° C. A 1 ml pipette containing 0.8 ml of 50% polyethylene glycol (PEG) 1500 (freshly prepared or kept in the dark) in medium D (pH 7.6–7.8 as indicated by phenol red) was used to suspend the cells gently while the solution was added over a period of 1 minute. The suspension was kept at 37° C. for 1 minute and 1 ml of medium D was added over another period of 1 minute. A further 20 ml of medium D was then added over a period of 5 minutes and the cells were centrifuged and gently resuspended in Dulbecco's modified medium (DMM) containing 20% FCS. The suspension was distributed in 48×2 ml wells in Linbro BCL-5041 trays. After 24 hours one half of the medium was replaced with HAT containing medium (Littlefield, Science, 1964, 145, 709). This operation was repeated in the two subsequent days and then every 2 days.

Vigorous growth in a well after 13–15 days was taken as showing a successful hybrid clone(s). Only six of the subcultures showed hybrid growth. The spent medium of each hybrid culture was tested by indirect haemagglutination of sheep red blood corpuscles (SRBC) which had been sensitised with different mouse monoclonal antibodies specific for SRBC by the following procedure: $2.5 \times 10^8$ SRBC were coated by incubation for 1 hour at room temperature with 5 ml of culture supernatants of anti-SRBC hybrid myelomas (Köhler and Milstein, European Journal of Immunology, 1976, 6, 511) minimally diluted to avoid agglutination. The coated SRBC were centrifuged down and the pellet resuspended in 2.5 ml of PBS. Aliquots of 25 µl were distributed in V-bottom microtiter trays and 25 µl of supernatant from the hybrid culture added to each well. After incubation for 1 hour the plate was centrifuged at 200 g for 4 minutes and then kept in a 45° slope for 30–60 minutes. In this way one culture (YA 2/40) was selected which was clearly positive when the SRBC were coated with Sp3 (an IgG1) but negative when coated with Sp2 (an IgG2b) or Sp1 (IgM). This positive hybrid was cloned in soft agar and eight individual clones were selected. All of these clones were found to be positive in the test with Sp3 coated SRBC. For each of the eight clones the antibody secreted by the clone was internally labelled by incubating the cells for 24 hours with $^{14}C$-lysine. The supernatants were then analysed as described by Köhler and Milstein, ibid, using sodium dodecyl sulphate polyacrylamide (10%) gel electrophoresis (SDS-PAGE) after total reduction, and isoelectric focusing (IEF). All clones appeared to be identical, revealing a heavy chain of about 50,000 MW and a single band present in the light chain zone (in contrast to the parent cell line which lacked the heavy chain band). It was not possible to demonstrate the presence of the two separate expected light chains (myeloma parental and antibody specific) probably due to their possessing similar mobilities. Three of the eight clones were cloned again to ensure purity and increase stability. One of the subclones, designated YA2/-4OH(LK) was selected for particular study of its properties as described below.

Properties of hybrid cell line YA2/4OH(LK)

Binding of the internally [$^3$H-Lys] labelled antibody YA2/40 to cells coated with different classes of anti-SRBC antibody showed that the hybrid recognised several mouse IgG but not three IgM myelomas. Binding to Sp1 (IgM) coated cells gave the same value as the background binding to uncoated cells whilst binding to Sp3 (Igg1) and Sp2 (Igg2) coated cells was 4.9 and 35 times background respectively, a difference which correlates with the number of antigenic sites recognised by Sp2 and Sp3 (the number of antigenic sites recognised by Sp1 being intermediate between Sp2 and Sp3).

Coating with Sp2 gives a sensitive procedure to assay for binding of [$^3$H]YA2/4OH(LK), and further specificity studies were done by inhibition of this binding. These studies confirmed that the hybrid recognised proteins from both the $\gamma 1$ and $\gamma 2$ subclasses of IgG. Inhibition by IgM was at least 50-fold less effective although at high concentrations of protein some inhibition was observed, probably due to IgG impurities in the preparation. Tests of inhibition with MOPC 21 and its variants IF1 (lacking the CH3 domain) and IF2 (lacking the CH1 domain), and also with the F (ab')$_2$ fragment of MOPC 21 (lacking the CH2 and CH3 domains), established that the antigenic determinant in the IgG1 is located in the CH1 region.

In species specificity tests the monoclonal antibody YA2/40 appeared to be completely negative towards human, horse or rat serum but showed some degree of cross-reaction to rabbit serum. On the other hand, it cross-reacted with guinea pig serum quite effectively. This pattern of cross-reaction between the different species of IgG indicates that the antigenic determinant involves a similarity of local structure in the guinea pig and the different mouse subclasses which, however, differ completely from the human, horse and rat.

Example 3

Production of hybrid between cell line I-078 and spleen cells from DA rat immunised with cells from AO rat A rat of the DA strain was immunised with cells from an AO rat using a similar procedure to that described in Example 2 for immunisation with mouse IgG. Spleen cells from the rat were then fused to the cell line I-078 again using a similar procedure to that described in Example 2, the culture being divided into 96 cells and being allowed to grow for four weeks in selective medium. The hybrids of the various cultures were analysed by their ability to secrete Ig different from the myeloma parent using SDS-PAGE analysis. The results obtained are shown in Table 1 given below.

TABLE 1

| Preferential fixation of the hybrid immunoglobulin secretion phenotype following fusion with the rat myeloma line | |
|---|---|
| Number of cultures | 96 |
| Cultures showing growth of hybrids | 17 |
| Number showing secretion of Y3-like light chain* | 11 |
| Number showing secretion of Ig chains different from Y3* | 11 |
| Number showing secretion of Y3 light chain in the absence of Ig chains* | 1 |

*Only 12 of the cultures showing hybrids were tested by SDS-PAGE analysis of secreted products since 5 of the cultures had an insufficient number of cells for a meaningful test.

Example 4

Production of hybrids between cell line I-078 and variously sensitized spleen cells Using a similar procedure to that described in Example 2 a variety of hybrid cell lines has been produced yielding antibodies against a range of targets including bone marrow cells, cells from neoplastic material, complement cells and drugs. These hybrids and the salient features of their preparation are summarised in Table 2 below. In this Table the various headings indicate the immunizing agent used to produce the sensitized spleen cells, the number of subcultures of hybrids showing active growth, the number of such subcultures which show positive activity against the immunizing agent, the number of clones isolated from these subcultures, and finally, the antibody target of these clones which generally corresponds to the sensitizing agent used.

TABLE 2

| Sensitizing agent | Successful growth | Positive cultures | Isolated clones | Antibody target |
|---|---|---|---|---|
| Human complement (C3) | 80/96 | 4–5 | 3 | Human complement (C3) |

TABLE 2-continued

| Sensitizing agent | Successful growth | Positive cultures | Isolated clones | Antibody target |
| --- | --- | --- | --- | --- |
| Mouse bone marrow cells | 62/64 | >35 | 21 | Mouse bone marrow cells |
| Human B cells (Daudi) | 96/96 | >30 | 6 (to date) | Human B cells (Daudi) |
| Human colon carcinoma | 7/48 | | 4 | 3 Human colon carcinoma |
| Protein coupled seratonin | 18/24 | | 1 | Isolation in progress Serotonin |

Example 5

In vivo production of monoclonal antibody against mouse IgG (1) YA/4OH(LK) cells produced as described in Example 2 are grown as solid tumours in F1 (Lou X DA) rats by subcutaneous injection of $5 \times 10^7$ cells. After about 10 days of tumour begins to become evident at the site of injection. When an animal begins to show signs of distress it is sacrificed by total bleeding from the arteries after total anaesthenia. The collected blood is allowed to clot for 30 minutes at 37° C. and the serum is then cleared by centrifugation. The yield of serum is typically between 5 and 10 ml per animal and contains 10 to 15 mg/ml of IgG measured by radial immunodiffusion which gave rise to a prominent myeloma band component in cellulose acetate electrophoresis.

(2) In a variant of the above procedure the tumour is grown as an ascitic tumour to provide both blood and ascitic fluid as a source of antibody. The tumour is produced by an intraperitoneal injection of 0.5 ml of pristane about 2 weeks before the intraperitoneal injection of $5 \times 10^7$ cells. When an animal begins to show signs of distress it is sacrificed, the blood collected and treated as above and ascitic fluid is taken from the dead animal after surgical exposure of the abdominal cavity. The yield of ascitic fluid is typically about 10 ml per animal and contains 5 to 10 mg/ml of IgG.

The serum and/or ascitic fluid obtained in (1) and (2) above may be purified further to a degree appropriate to their intended use by means of known procedures described in the art, for example by the procedures described in Example 6.

Example 6

In vitro production of monoclonal antibody against mouse IgG

YA2/4OH(LK) cells produced as described in Example 2 are adapted to grow in the presence of a minimal amount of serum (5% or less). Once adapted, the cells are grown in 5 liter spinner flasks containing Eagle's minimum essential medium, Dulbecco's modification supplemented with 5% foetal calf serum and an atmosphere of 10% $CO_2$-90% air. The cells are grown until they reach the stationary phase(1) when the suspension contains from 10 to 50 µg of antibody per ml.
(1) In a variant of the above procedure the cells are grown in logarithmic phase with a minimum serum concentration and are then directly diluted with medium which contains no serum but does contain growth additives such as those recommended by Iscove.

In order to purify the antibody preparation(2), ammonium sulphate is added to the suspension to produce 50% saturation and the resulting precipitate is collected. The precipitate is dissolved in a minimum volume of phosphate buffered saline and the solution is dialysed against the same medium to produce a purified antibody preparation.
(2) In a further variant of the above procedure the purification procedure is continued using DEAE chromatography or immunoadsorbents, for example anti-rat immunoglobulin, or alternatively the procedure described is replaced by the use of membrane filters.

We claim:

1. A substantially pure rat myeloma cell line having the C.N.C.M. designation I-078.

2. A hybrid cell line prepared from cells of the cell line C.N.C.M. I-078 through the fusion thereof with immunocyte cells from an animal sensitized to an immunogen in a nutrient medium for said cells, followed by isolation of the hybrid cell line from the resultant mixture of cells.

3. An in vitro cell culture system comprising a substantially pure rat myeloma cell line designated C.N.C.M. I-078 in a nutrient medium therefor.

4. A cell fusion system which comprises cells of the cell line C.N.C.M. I-078 and immunocyte cells from an animal sensitized to an immunogen in a nutrient culture medium therefor together with an agent which promotes the fusion of said cells.

5. The cell fusion system according to claim 4, in which the immunocyte cells are spleen cells.

6. The cell fusion system according to claim 4, in which the immunocyte cells are rat cells.

7. The cell fusion system according to claim 4, in which the agent which promotes the fusion is polyethylene glycol.

8. The cell fusion system according to claim 4 which comprises cells of the cell line C.N.C.M. I-078 and spleen cells from a rat sensitized to an immunogen in a nutrient culture medium therefor together with polyethylene glycol.

9. A process for producing the hybrid cell line of claim 2, which comprises fusing cells of the cell line C.N.C.M. I-078 with immunocyte cells from an animal sensitized to an immunogen using an agent which promotes the fusion of said cells.

10. The process according to claim 9, in which the animal is sensitized to the immunogen by administration of the immunogen thereto.

11. A process for the production of antibodies which comprises culturing cells of the cell line of claim 2 in an in vitro or in vivo culture medium therefor and thereafter isolating the antibodies from said medium.

12. An antibody production process which comprises preparing the hybrid cell line of claim 2 by the fusion of cells of the cell line C.N.C.M. I-078 with immunocyte cells sensitized to an immunogen and culturing the hybrid cell line in an in vitro or in vivo culture medium therefor to produce antibodies against the sensitizing immunogen.

13. The process according to claim 12, in which the immunocyte cells are sensitized to the immunogen by the administration of the immunogen to an animal from which the immunocyte cells are obtained.

14. The process according the claim 13, in which the animal from which the immunocyte cells are obtained is a rat.

15. The process according to claim 11 in which cells of the hybrid cell line are cultured by inoculating a rat with the cell line to thereby produce a solid or ascitic tumor, and thereafter isolating the antibodies from the serum or ascitic fluid of the rat.

* * * * *